(12) United States Patent
Chen et al.

(10) Patent No.: US 10,345,568 B2
(45) Date of Patent: Jul. 9, 2019

(54) MUELLER-MATRIX MICROSCOPE AND MEASUREMENT AND CALIBRATION METHODS USING THE SAME

(71) Applicant: Wuhan Eoptics Technology Co., Ltd., Wuhan (CN)

(72) Inventors: Xiuguo Chen, Wuhan (CN); Jun Chen, Wuhan (CN); Chao Chen, Wuhan (CN); Shiyuan Liu, Wuhan (CN)

(73) Assignee: WUHAN EOPTICS TECHNOLOGY CO., LTD., Wuhan (CN)

( * ) Notice: Subject to any disclaimer, the term of this patent is extended or adjusted under 35 U.S.C. 154(b) by 43 days.

(21) Appl. No.: 15/487,407

(22) Filed: Apr. 13, 2017

(65) Prior Publication Data

US 2018/0164566 A1    Jun. 14, 2018

(30) Foreign Application Priority Data

Dec. 12, 2016 (CN) .......................... 2016 1 1140741

(51) Int. Cl.
*G02B 21/36* (2006.01)
*G02B 21/00* (2006.01)
(Continued)

(52) U.S. Cl.
CPC ......... *G02B 21/0092* (2013.01); *G01N 21/21* (2013.01); *G02B 6/42* (2013.01); *G02B 21/361* (2013.01); *G02B 21/367* (2013.01); *G02F 1/0027* (2013.01); *G02F 1/0045* (2013.01); *G01N 2201/0683* (2013.01); *G02B 5/3083* (2013.01); *G02B 26/0816* (2013.01)

(58) Field of Classification Search
CPC .... G02B 21/0092; G02B 21/367; G02B 6/42; G02B 21/361; G02B 26/0816; G02B 5/3083; G01N 21/21; G01N 2201/0683; G01N 2201/12; G02F 1/0027; G02F 1/0045
USPC ........................................... 348/79
See application file for complete search history.

(56) References Cited

U.S. PATENT DOCUMENTS 5,917,562 A *  6/1999  Woodgate .............. G02B 27/26
                                                          349/15
8,323,772 B2* 12/2012  Lin ........................ B82Y 20/00
                                                          359/599
(Continued)

OTHER PUBLICATIONS

Jesacher et al, Multi-focal light microscopy using liquid crystal spatial light modulators (Year: 2012).*

*Primary Examiner* — Shan E Elahi
(74) *Attorney, Agent, or Firm* — Matthias Scholl P.C.; Matthias Scholl

(57) ABSTRACT

A Mueller-matrix microscope, including: a polarizing unit and an analyzing unit. The polarizing unit is configured to modulate a light beam emitted from an external light source module to yield a polarized light beam, and then to project the polarized light beam on the surface of a sample to be measured. The analyzing unit is configured to analyze the polarization state of a light beam reflected from the surface of the sample, to acquire information of the sample. The analyzing unit includes a polarization state analyzer (PSA) and a backside reflection suppression (BRS) unit. The PSA unit is configured to demodulate the polarization state of the light beam; and the BRS unit is configured to suppress the backside reflections from transparent substrate.

9 Claims, 6 Drawing Sheets

(51) Int. Cl.
    *G02F 1/00*     (2006.01)
    *G02B 6/42*     (2006.01)
    *G01N 21/21*     (2006.01)
    *G02B 5/30*     (2006.01)
    *G02B 26/08*     (2006.01)

(56) References Cited

U.S. PATENT DOCUMENTS

| | | | |
|---|---|---|---|
| 9,903,934 B2 * | 2/2018 | Antoina | G01S 17/66 |
| 2009/0303571 A1 * | 12/2009 | Sandstrom | G02B 5/1809 |
| | | | 359/291 |
| 2010/0152052 A1 * | 6/2010 | Goodman | G01N 1/36 |
| | | | 506/7 |
| 2013/0169706 A1 * | 7/2013 | Harant | H04N 9/3111 |
| | | | 345/697 |
| 2013/0265576 A1 * | 10/2013 | Acher | G01J 4/00 |
| | | | 356/369 |
| 2014/0106980 A1 * | 4/2014 | Schubert | G01N 21/23 |
| | | | 506/9 |
| 2014/0192355 A1 * | 7/2014 | Froigneux | G01N 21/211 |
| | | | 356/301 |
| 2017/0003372 A1 * | 1/2017 | Antoina | G01S 17/66 |
| 2017/0108528 A1 * | 4/2017 | Atlas | G01B 11/002 |

* cited by examiner

MUELLER-MATRIX MICROSCOPE AND MEASUREMENT AND CALIBRATION METHODS USING THE SAME

CROSS-REFERENCE TO RELATED APPLICATIONS

Pursuant to 35 U.S.C. § 119 and the Paris Convention Treaty, this application claims the benefit of Chinese Patent Application No. 201611140741.5 filed Dec. 12, 2016, the contents of which are incorporated herein by reference. Inquiries from the public to applicants or assignees concerning this document or the related applications should be directed to: Matthias Scholl P. C., Attn.: Dr. Matthias Scholl Esq., 245 First Street, 18th Floor, and Cambridge, Mass. 02142.

BACKGROUND OF THE INVENTION

Field of the Invention

The invention relates to a back focal plane Mueller-matrix microscope.

Description of the Related Art

In recent years, two-dimensional (2D) materials have been developed and continue to attract much attention. Optical measurement and characterization techniques have become increasingly important for the study and application of these structures.

Commonly, nanoscale measurement utilizes scanning electron microscope (SEM), atomic force microscope (AFM) and transmission electron microscope (TEM). SEM and TEM work in vacuum and the samples are destroyed in the process, so SEM and TEM are not ideal. On the other hand, AFM is slow to scan, and is incapable of characterizing optical constants of the samples.

Conventional optical microscopy techniques solve the above disadvantages; however, they are inapplicable in characterizing thicknesses of thin film. In addition, conventional ellipsometry is relatively inconvenient to suppress backside reflections from transparent substrates or solid-liquid interfaces, leading to low measurement accuracy.

SUMMARY OF THE INVENTION

In view of the above-described problems, it is one objective of the invention to provide a Mueller-matrix microscope capable of phase modulation using liquid crystal devices. The Mueller-matrix microscope comprises a backside reflection suppression (BRS) unit, and is capable of measuring the d thin film and two-dimensional (2D) materials accurately with high resolution in a wide field-of-view (FOV), by combining ellipsometry with optical microscopy techniques.

To achieve the above objective, in accordance with one embodiment of the invention, there is provided a Mueller-matrix microscope capable of phase modulation using liquid crystal devices, the ellipsometer comprising: a polarizing unit and an analyzing unit.

In a class of this embodiment, the polarizing unit is configured to modulate a polarization state of a light beam emitted from an external light source module to yield a polarized light beam, and the polarized light beam is projected on a surface of a sample.

In a class of this embodiment, the analyzing unit is configured to analyze the polarization state of the light beam reflected from the surface of the sample, and information of the sample is obtained.

In a class of this embodiment, the polarizing unit comprises a first lens, an aperture diaphragm, a plane mirror, a polarization state generator (PSG), a beam splitter, a second lens, and an objective lens. The light beam emitted from the external light source module is collimated by the first lens to yield a parallel light beam. The parallel light beam is allowed to pass through the aperture diaphragm, and is specularly reflected by the plane mirror. The light beam enters the PSG, and the polarization state of the light beam is modulated to yield the polarized light beam. The polarized light beam is allowed to pass through: the beam splitter, the second lens, and the objective lens, in that order, and is projected on the surface of the sample.

In a class of this embodiment, the PSG comprises a polarizer, a first ferroelectric liquid crystal device, a first quarter-wave plate, and a second ferroelectric liquid crystal device. The polarizer, the first ferroelectric liquid crystal device, the first quarter-wave plate, and the second ferroelectric liquid crystal device are disposed coaxially along a direction of an optical path in that order.

In a class of this embodiment, the plane mirror is disposed on a rotating table. The plane mirror is driven by the rotating table to rotate, so that off axes of light beam focal positions are gathered at the back focal plane of the objective lens, and an angle of incidence of the light beam projected from the objective lens to the surface of the sample is close to the Brewster angle of the sample, thus facilitating the measurement of polarization state.

In a class of this embodiment, the beam splitter is configured to reflect the light beam in the polarizing unit so as to change a direction of propagation of the light beam. meanwhile, the light beam is allowed to penetrate through the beam splitter in the analyzing unit. The beam splitter is a non-polarization beam splitter.

In a class of this embodiment, the analyzing unit comprises a polarization state analyzer (PSA) and a backside reflection suppression unit. The light beam reflected from the surface of the sample is collected by the objective lens, and is allowed to pass through: the second lens, the beam splitter, the PSA, and the BRS unit, in that order, and enters a camera. The PSA is configured to demodulate the polarization state of the light beam. The BRS unit is configured to suppress the backside reflections from transparent substrate, so as to improve the measurement accuracy of the Mueller-matrix microscope.

In a class of this embodiment, the PSA comprises a third ferroelectric liquid crystal device, a second quarter-wave plate, a fourth ferroelectric liquid crystal device, and an analyzer. The third ferroelectric liquid crystal device, the second quarter-wave plate, the fourth ferroelectric liquid crystal device, and the analyzer are disposed coaxially along a direction of an optical path in that order.

In a class of this embodiment, the BRS unit comprises a third lens, a pinhole, and a fourth lens. The third lens, the pinhole, and the fourth lens are disposed coaxially. Focal lengths of the third lens and the fourth lens are conjugate. The pinhole is disposed at the conjugate focus of the third lens and the fourth lens. The pinhole has an appropriate aperture, so as to suppress backside reflections from transparent substrates or solid-liquid interfaces, thus improving the measurement accuracy of the ellipsometer.

In a class of this embodiment, the external light source module comprises a light source, a wavelength selector, an optical fiber coupler, and an output optical fiber. The light source is connected to the wavelength selector and the optical fiber coupler via fibers. The light beam generated by the light source is selected by the wavelength selector to yield a single-wavelength light beam. The single-wavelength light beam is transmitted to the output optical fiber via the optical fiber coupler. The output optical fiber is used as an output end of the external light source module.

It is another objective of the invention to provide a method for measuring the sample using the Mueller-matrix microscope, comprising:

1) placing the sample at a sample stage; regulating the polarizing unit and the analyzing unit to obtain a clear image of a certain area of the sample at a camera;
2) collimating the single-wavelength light beam emitted from the external light source module to yield the parallel light beam; modulating the parallel light beam using the PSG to yield polarized light; and projecting the polarized light on the surface of the sample;
3) demodulating the light beam reflected from the surface of the sample using the PSA; and allowing the light beam to enter the camera to obtain different intensity signals of reflected light under different polarization states;
4) calculating measured Mueller-matrix data of the sample at each pixel on the camera according to the intensity signals in 3), where all of the measured Mueller-matrix data at each pixel forms measured Mueller-matrix data of the sample in an entire field of view (FOV);
5) changing a wavelength $\lambda$ and the angle of incidence $\theta$ of the light beam; rotating the sample stage to alter the azimuth angle $\phi$ between the light beam and the sample; repeating 2)-4), and calculating the measured Mueller-matrix data under different wavelengths $\lambda$, different angles of incidence $\theta$, and different azimuth angles $\phi$;
6) calculating theoretical Mueller-matrix data of the sample according to the Fresnel formula based on a given configuration of the wavelength $\lambda$, the angle of incidence $\theta$, and the azimuth angle $\phi$;
7) fitting the measured Mueller-matrix data to obtain actual Mueller-matrix data of the sample; comparing the actual Mueller-matrix data with the theoretical Mueller-matrix data: when a deviation falls within a given range, confirming the actual Mueller-matrix data is accurate; calculating parameter values of the sample at each pixel according to the actual Mueller-matrix data; calculating parameter values of the sample at all pixels to obtain a three-dimensional microstructure of the sample in the entire FOV; when the deviation is out of the given range, repeating 2)-6) until the deviation between the actual Mueller-matrix data and the theoretical Mueller-matrix data falls within the given range, obtaining the three-dimensional microstructure of the sample.

Advantages of the Mueller-matrix microscope according to embodiments of the invention are summarized as follows:

1. The Mueller-matrix microscope combines the ellipsometry technique with the optical microscope technique, and uses the vertical objective lens imaging, thus a high lateral resolution of the optical microscope at its optical limit is achieved by the ellipsometer, meanwhile, a vertical resolution at 1 Å magnitude of ellipsometry technique is inherited. Due to the design of vertical objective lens imaging, the problems as small focal depth and narrow FOV of illumination-tilted specular-reflection imaging system are fundamentally avoided, and a high-resolution, wild FOV measurement of geometric parameters of the thin film is realized.

2. A polarization measurement system capable of phase modulation using ferroelectric liquid crystal devices is used, thus all of the optical motion elements in the optical path are eliminated, and higher measurement accuracy is achieved; possibly, sixteen Mueller-matrix elements of the sample can be obtained by one measurement.

3. The wavelength selector and the plane mirror are used, thus a measurement under conditions of broadband spectrum and multi-incident angles is realized.

4. The ellipsometer comprises the BRS unit which effectively suppress backside reflections from transparent substrates or solid-liquid interfaces, thus the signal-to-noise ratio (SNR) is improved. Because the measured Mueller-matrix data at each pixel is independently measured, and the parameter value of the sample on each pixel is obtained, the three-dimensional microstructure of the sample in the entire FOV is accurately real-timely reconstructed.

5. The measurement apparatus and measurement method in the embodiments of the invention belong to the optical measurement technique which has advantages as contactless, high-resolution, wide FOV, rapid, non-destructive, and accurate, therefore, the ellipsometer can find wide applications in the preparation and application of new materials such as two-dimensional (2D) materials.

BRIEF DESCRIPTION OF THE DRAWINGS

The invention is described herein below with reference to the accompanying drawings, in which.

DETAILED DESCRIPTION OF THE EMBODIMENTS

For further illustrating the invention, experiments detailing a Mueller-matrix ellipsometer capable of phase modulation using liquid crystal devices are described below. It should be noted that the following examples are intended to describe and not to limit the invention.

Figure 1:
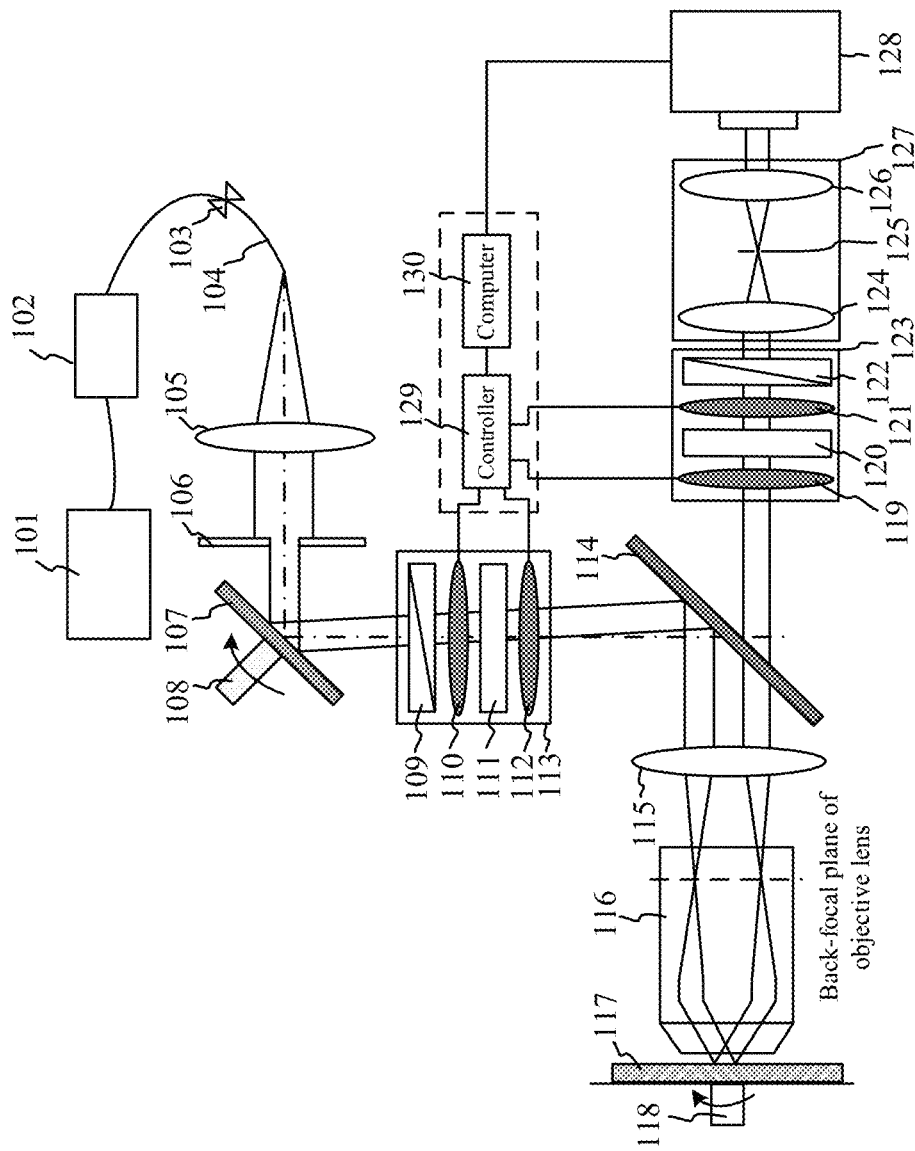
FIG. 1 is a schematic diagram of a Mueller-matrix microscope capable of phase modulation using liquid crystal devices in accordance with one embodiment of the invention.

As shown in FIG. 1, the back focal plane Mueller-matrix microscope capable of phase modulation using liquid crystal devices comprises a light source 101, a wavelength selector 102, a fiber coupler 103, an output optical fiber 104, a first lens 105, an aperture diaphragm 106, a plane mirror 107, a rotating table 108, a polarizer 109, a first ferroelectric liquid crystal device 110, a first quarter-wave plate 111, a second ferroelectric liquid crystal device 112, a PSG 113, a beam splitter 114, a second lens 115, an objective lens 116 (a preferable numerical aperture thereof is 0.95), a sample 117, a sample stage 118, a third ferroelectric liquid crystal device 119, a second quarter-wave plate 120, a fourth ferroelectric liquid crystal device 121, an analyzer 122, a PSA 123, a third lens 124, a pinhole 125, a fourth lens 126, a BRS unit 127, a camera 128, a controller 129, and a computer 130.

The back focal plane Mueller-matrix microscope comprises a polarizing unit and an analyzing unit.

The polarizing unit is configured to modulate a polarization state of a light beam emitted from an external light source module to yield a polarized light beam, and the polarized light beam is projected on the surface of the sample 117.

The analyzing unit is configured to analyze the polarization state of the light beam reflected from the surface of the sample 117, and information of the sample 117 is obtained.

The polarizing unit comprises the first lens 105, the aperture diaphragm 106, the plane mirror 107, the PSG 113, the beam splitter 114, the second lens 115, and the objective lens 116. The light beam emitted from the external light source 101 module is collimated by the first lens 105 to yield a parallel light beam. The parallel light beam is allowed to pass through the aperture diaphragm 106, and is specularly reflected by the plane mirror 107. The light beam enters the PSA 113, and the polarization state of the light beam is modulated to yield the polarized light beam. the polarized light beam is allowed to pass through: the beam splitter 114, the second lens 115, and the objective lens 116, in that order, and is projected on the surface of the sample 117.

The PSG 113 comprises the polarizer 109, the first ferroelectric liquid crystal device 110, the first quarter-wave plate 111, and the second ferroelectric liquid crystal device 112. The polarizer, the first ferroelectric liquid crystal device, the first quarter-wave plate, and the second ferroelectric liquid crystal device are disposed coaxially along a direction of an optical path in that order.

The plane mirror 107 is disposed on the rotating table 108. The plane mirror 107 is driven by the rotating table 108 to rotate, so that off axes of light beam focal positions are gathered at the back focal plane of the objective lens 116, and an angle of incidence of the light beam projected from the objective lens 116 to the surface of the sample is close to the Brewster angle of the sample 117, thus facilitating the measurement of polarization state.

The beam splitter 114 is configured to reflect the light beam in the polarizing unit so as to change a direction of propagation of the light beam, meanwhile, the light beam is allowed to penetrate through the beam splitter in the analyzing unit. The beam splitter 114 is a non-polarization beam splitter 114, and a splitting ratio thereof is 50:50.

The analyzing unit comprises the PSA 123 and the BRS unit 127. The light beam reflected from the surface of the sample 117 is collected by the objective lens 116, and passes through: the second lens 115, the beam splitter 114, the PSA 123, and the BRS unit 127, in that order, and enters a camera 128. The PSA 123 is configured to demodulate the polarization state of the light beam. The BRS unit 127 is configured to suppress backside reflections from transparent substrates or solid-liquid interfaces, so as to improve the measurement accuracy of the ellipsometer.

The PSA 123 comprises a third ferroelectric liquid crystal device 119, a second quarter-wave plate 120, a fourth ferroelectric liquid crystal device 121, and an analyzer 122. The third ferroelectric liquid crystal device, the second quarter-wave plate, the fourth ferroelectric liquid crystal device, and the analyzer are disposed coaxially along a direction of an optical path in that order.

The BRS unit 127 comprises a third lens 124, a pinhole 125, and a fourth lens 126. The third lens, the pinhole, and the fourth lens are disposed coaxially. Focal lengths of the third lens 124 and the fourth lens 126 are conjugate. The pinhole 125 is disposed at a conjugate focus of the third lens 124 and the fourth lens 126. The pinhole 125 has an appropriate aperture, so as to suppress backside reflections from transparent substrates or solid-liquid interfaces, thus improving the signal-to-noise ratio (SNR) and the measurement accuracy of the ellipsometer.

The external light source module comprises the light source 101, the wavelength selector 102, the optical fiber coupler 103 and the output optical fiber 104. The light source 101 is connected to the wavelength selector 102 and the optical fiber coupler 103 via fibers. The light beams generated by the light source 101 are selected by the wavelength selector 102 to yield a single-wavelength light beam. The single-wavelength light beam is transmitted to the output optical fiber 104 via the optical fiber coupler 103. The output optical fiber 104 is used as an output end of the external light source module.

The light source 101, the wavelength selector 102, and the optical fiber coupler 103 are disposed at the same light path, and are connected via fibers. One end of the output optical fiber 104 is connected to the optical fiber coupler 103. The light beam output from the other end of the output optical fiber 104 is at the focal position of the first lens 105, and a single-wavelength parallel light beam is yielded. The light beam experiences beam constraint of aperture diaphragm 106, and is reflected by the plane mirror 107 disposed on the rotating table 108. Then the light beam is modulated in the PSG 113.

The PSG 113 comprises the polarizer 109, the first ferroelectric liquid crystal device 110, the first quarter-wave plate 111, and the second ferroelectric liquid crystal device 112. The polarizer, the first ferroelectric liquid crystal device, the first quarter-wave plate, and the second ferroelectric liquid crystal device are disposed coaxially along a direction of an optical path in that order. The polarized light beam is reflected and transmitted by the beam splitter 114 and passes through the second lens 115, then the light beam is gathered at the back focal plane of the objective lens 116. The rotating table 108 is adjusted, thus an angle of inclination of the plane mirror 107 is controlled, and an angle of incidence of the light beam projected from the objective lens 116 to the surface of the sample is close to the Brewster angle of the sample 117.

The light beam reflected from the surface of the sample 117 is collected by the objective lens 116, and passes through: the second lens 115, the beam splitter 114, the PSA 123, and the BRS unit 127, in that order, and enters a camera 128. The PSA 123, the BRS unit 127, and the camera 128 are disposed coaxially. The light beam is allowed to penetrate through the beam splitter 114, and is analyzed in the PSA 123, then the light beam enters the BRS unit 127 thereby suppressing the backside reflections from transparent substrates or solid-liquid interfaces.

The PSA 123 comprises the third ferroelectric liquid crystal device 119, the second quarter-wave plate 120, the fourth ferroelectric liquid crystal device 121, and the analyzer 122. The third ferroelectric liquid crystal device, the second quarter-wave plate, the fourth ferroelectric liquid crystal device, and the analyzer are disposed coaxially along the direction of an optical path in that order. The BRS unit 127 comprises the third lens 124, the pinhole 125, and the fourth lens 126. The third lens 124, the pinhole 125, and the fourth lens 126 are disposed coaxially. Focal length of the third lens 124 and the fourth lens 126 are conjugate. The pinhole 125 is disposed at the conjugate focus of the third lens 124 and the fourth lens 126. A camera 128 is disposed at a back focal plane of the fourth lens 126, so that a clear image of the sample 117 is formed.

The computer 130 controls the phases of the first ferroelectric liquid crystal device 110 and the second ferroelectric liquid crystal device 112 in the PSG 113, and the phases of the third ferroelectric liquid crystal device 119 and the fourth ferroelectric liquid crystal device 121 in the PSA 123 via the controller 129, thus multiple polarization states are modulated and analyzed.

A method for obtaining geometric parameters of nanostructured thin film and two-dimensional (2D) materials using the back focal plane Mueller-matrix microscope the following steps:

1) The sample 117 is placed at the sample stage 118; the polarizing unit and the analyzing unit are regulated until a clear image of a certain area of the sample 117 at the camera 128 is obtained; the sample stage 118 can drive the sample 117 to rotate.

2) The light beam emitted from the light source 101 is collimated by the wavelength selector 102 and the first lens 105 to yield collimated monochromatic light beam; the collimated monochromatic light beam is allowed to pass through the aperture diaphragm 106 and the plane mirror 107, and is modulated by the polarization generation unit 113 to yield polarized light beam; the direction of propagation of the polarized light beam is changed by the beam splitter 114; the light beam passes through the second lens 115 and is gathered at the back focal plane of the objective lens 116; and the light beam is projected on the surface of the sample 117 via the objective lens 116.

3) The light beam is reflected from the surface of the sample 117 and collected by the high numerical aperture objective lens 116; the light beam passes through the second lens 115, the beam splitter 114, the PSA 123, and the BRS unit 127 in that order and enters the camera 128; intensity signals of the reflected light is collected by the camera 128; four ferroelectric liquid crystal devices in the PSG 113 and in the PSA 123 are controlled to collect intensity signals of reflected lights under different polarization states.

4) Measured Mueller-matrix data at each pixel on the camera 128 is calculated according to the intensity signals in 3); all of the measured Mueller-matrix data at each pixel forms measured Mueller-matrix data of the sample 117 in an entire FOV.

Data acquisition principle at any pixel on the camera 128 is identical, specifically, take the data acquisition at the pixel which is on arbitrary line m and row n of the camera 128 as an example: a relationship between the Stokes vectors $S_{out}$ of the reflected light beam and the Stokes vectors $S_{in}$ of the incident light beam is shown as Formula (1):

$$S_{out}=[M_A R(\theta_A)] \cdot M(\theta_{F4},\delta_{F4}) \cdot M(\theta_{C2},\delta_{C2}) \cdot M(\theta_{F3},\delta_{F3}) \cdot M_S \cdot M(\theta_{F2},\delta_{F2}) \cdot M(\theta_{C1},\delta_{C1}) \cdot M(\theta_{F1},\delta_{F1}) \cdot [R(-\theta_P) M_P] \cdot S_{in} \quad (1)$$

where, $M_P$, $M_A$, $M(\theta_{F1}, \delta_{F1})$, $M(\theta_{F2}, \delta_{F2})$, $M(\theta_{F3}, \delta_{F3})$, $M(\theta_{F4}, \delta_{F4})$, $M(\theta_{C1}, \delta_{C1})$, and $M(\theta_{C2}, \delta_{C2})$ are corresponding Mueller matrixes of the polarizer 109, the analyzer 122, the first ferroelectric liquid crystal device 110, the second ferroelectric liquid crystal device 112, the third ferroelectric liquid crystal device 119, the fourth ferroelectric liquid crystal device 121, the first quarter-wave plate 111, and the second quarter-wave plate 120. $\theta_P$ and $\theta_A$ are angles between a direction of transmission axis and a plane of incidence of the polarizer 109 and the analyzer 122. $\theta_{C1}$, $\theta_{C2}$, $\theta_{F1}$, $\theta_{F2}$, $\theta_{F3}$, and $\theta_{F4}$ are angles between a direction of fast axis and a plane of incidence of the first quarter-wave plate 111, the second quarter-wave plate 120, the first ferroelectric liquid crystal device 110, the second ferroelectric liquid crystal device 112, the third ferroelectric liquid crystal device 119, and the fourth ferroelectric liquid crystal device 121. During the data acquisition, azimuth angles of the fast axes of the first quarter-wave plate 111, the second quarter-wave plate 120, the first ferroelectric liquid crystal device 110, the second ferroelectric liquid crystal device 112, the third ferroelectric liquid crystal device 119, and the fourth ferroelectric liquid crystal device 121 are fixed. $\delta_{C1}$, $\delta_{C2}$, $\delta_{F1}$, $\delta_{F2}$, $\delta_{F3}$, and $\delta_{F4}$ are corresponding phase retardations of first quarter-wave plate 111, the second quarter-wave plate 120, the first ferroelectric liquid crystal device 110, the second ferroelectric liquid crystal device 112, the third ferroelectric liquid crystal device 119, and the fourth ferroelectric liquid crystal device 121. Practically, $\delta_{C1}$ and $\delta_{C2}$ generally varies with wavelength, thus a composite wave plate which is a composite of a plurality of wave plates is adopted so that within the given wavelength range the variations of $\delta_{C1}$ and $\delta_{C2}$ are as small as possible. The alignment of the composite wave plate can refer to the Chinese patent CN393555A which disclosed a method and a device for aligning optical axis of a composite wave plate.

In an ideal system, $M_S$ represents a Mueller matrix of the sample 117. In an actual system of measurement device, due to Mueller matrixes of non-ideal beam splitter 114 and objective lens 116, an expression of $M_S$ is shown in Formula (2):

$$M_S = M_r^{BS'} \cdot M_{id}^{OB} \cdot M'_S \cdot M_{rd}^{OB} \cdot M_t^{BS'} \quad (2)$$

where, $M_S$ represents a Mueller-matrix product of the sample 117, the beam splitter 114, and the objective lens 116; $M_r^{BS'}$ is the measured Mueller matrix of the beam splitter 114 when the beam splitter is configured to reflect the light beam; $M_{id}^{OB}$ is the Mueller matrix of the objective lens 116 when the objective lens is in the incident light path; $M'_S$ is the real Mueller matrix of the sample 117; $M_{rd}^{OB}$ is a Mueller matrix of the objective lens 116 when the objective lens is configured to collect the reflected light beam; and $M_t^{BS'}$ is the measured Mueller matrix of the beam splitter 114 when the beam splitter allows the light beam to penetrate through. Calculation processes of $M_r^{BS'}$, $M_{id}^{OB}$, $M_{rd}^{OB}$, and $M_t^{BS'}$ are illustrated in the following in situ calibration example of the beam splitter 114 and the following in situ calibration example of the objective lens 116. After values of $M_r^{BS'}$, $M_{id}^{OB}$, $M_{rd}^{OB}$ and $M_t^{BS'}$ are obtained in the examples, and $M_S$ is obtained according to the Formula (1), the real Mueller matrix of the sample 117 is calculated according to the Formula (2).

An intensity expression of the reflected light beam is obtained by simplifying the Formula (1), and is shown as Formula (3):

$$I = I_0 \{ H_1 + c_A(K_{F4} K_{C2}(K_{F3} H_2 + N_{F3} H_3 - G_{F3} H_4) + \\
N_{C2} N_{F3} H_2 + V_{F3} H_3 + L_{F3} H_4) - \\
G_{C2}(G_{F3} H_2 - L_{F3} H_3 + \cos\delta_{F3} H_4) + \\
N_{F4} N_{C2}(K_{F3} H_2 + N_{F3} H_3 - G_{F3} H_4) + \\
V_{C2} N_{F3} H_2 + V_{F3} H_3 + L_{F3} H_4) + \\
L_{C2}(G_{F3} H_2 - L_{F3} H_3 + \cos\delta_{F3} H_4) - \\
G_{F4} G_{C2}(K_{F3} H_2 + N_{F3} H_3 - G_{F3} H_4) - \\
L_{C2}(N_{F3} H_2 + V_{F3} H_3 + L_{F3} H_4) + \\
\cos\delta_{C2}(G_{F3} H_2 - L_{F3} H_3 + \cos\delta_{F3} H_4)) + \quad (3)$$

-continued
$$s_A(N_{F4}K_{C2}(K_{F3}H_2 + N_{F3}H_3 - G_{F3}H_4) +$$
$$N_{C2}(N_{F3}H_2 + V_{F3}H_3 + L_{F3}H_4) -$$
$$G_{C2}(G_{F3}H_2 - L_{F3}H_3 + \cos\delta_{F3}H_4) +$$
$$V_{F4}N_{C2}(K_{F3}H_2 + N_{F3}H_3 - G_{F3}H_4) +$$
$$V_{C2}(N_{F3}H_2 + V_{F3}H_3 + L_{F3}H_4) +$$
$$L_{C2}(G_{F3}H_2 - L_{F3}H_3 + \cos\delta_{F3}H_4) +$$
$$L_{F4}G_{C2}(K_{F3}H_2 + N_{F3}H_3 - G_{F3}H_4) -$$
$$L_{C2}(N_{F3}H_2 + V_{F3}H_3 + L_{F3}H_4) +$$
$$\cos\delta_{C2}(G_{F3}H_2 - L_{F3}H_3 + \cos\delta_{F3}H_4))\}$$

where, an expression of $H_i$ in the Formula (3) is shown in Formula (4):

$$H_i = M_{i1} + M_{i2}(N_{F2}K_{C1}(c_P K_{F1} + s_P N_{F1}) + \tag{4}$$
$$N_{C1}(c_P N_{F2} + s_P V_{F1}) - G_{C1}(c_P G_{F1} - s_P L_{F1}) +$$
$$N_{F2}N_{C1}(c_P K_{F1} + s_P N_{F1}) + V_{C1}(c_P N_{F1} + s_P V_{F1}) +$$
$$L_{C1}(c_P G_{F1} - s_P L_{F1}) - G_{F2}G_{C1}(c_P K_{F1} + s_P N_{F1}) -$$
$$L_{C1}(c_P N_{F1} + s_P V_{F1}) + \cos\delta_{C1}(c_P G_{F1} - s_P L_{F1})) +$$
$$M_{i3}(N_{F2}K_{C1}(c_P K_{F1} + s_P N_{F1}) + N_{C1}(c_P N_{F1} + s_P V_{F1}) -$$
$$G_{C1}(c_P G_{F1} - s_P L_{F1}) + V_{F2}N_{C1}(c_P K_{F1} + s_P N_{F1}) +$$
$$V_{C1}(c_P N_{F1} + s_P V_{F1}) + L_{C1}(c_P G_{F1} - s_P L_{F1}) +$$
$$L_{F2}G_{C1}(c_P K_{F1} + s_P N_{F1}) - L_{C1}(c_P N_{F1} + s_P V_{F1}) +$$
$$\cos\delta_{C1}(c_P G_{F1} - s_P L_{F1})) + M_{i4}(G_{F2}K_{C1}(c_P K_{F1} + s_P N_{F1}) +$$
$$N_{C1}(c_P N_{F1} + s_P V_{F1}) - GC_{F1}(c_P G_{F1} - s_P L_{F1}) -$$
$$L_{F2}N_{C1}(c_P K_{F1} + s_P N_{F1}) + V_{C1}(c_P N_{F1} + s_P V_{F1}) +$$
$$L_{C1}(c_P G_{F1} - s_P L_{F1}) + \cos\delta_{F2}G_{C1}(c_P K_{F1} + s_P N_{F1}) -$$
$$L_{C1}(c_P N_{F1} + s_P V_{F1}) + \cos\delta_{C1}(c_P G_{F1} - s_P L_{F1}))$$

where, $K_i=c_i^2+s_i^2\cos\delta_i$, $N_i=c_i s_i(1-\cos\delta_i)$, $V_i=s_i^2+c_i^2\cos\delta_i$, $L_i=c_i\sin\delta_i$, $G_i=s_i\sin\delta_i$, $s_i=\sin(2\theta_i)$, and $c_i=\cos(2\theta)$; and $K_i$, $N_i$, $V_i$, $L_i$, $G_i$, $s_i$, and $c_i$ are all intermediate variable; $I_0$ is the intensity value before the polarizer 109 is input; I is the intensity value actually measured by the camera 128 which is at the rear end of the measurement system; $M_{jk}$ is an element in the Mueller matrix $M_S$ (where i is C1, C2, F1. F2. F3, F4, A, or P, and j, k=1, 2, 3, or 4).

Existing ferroelectric liquid crystal device has two different phases: ferroelectric phase and paraelectric phase. The computer 130 controls the phase change of the four ferroelectric liquid crystal devices via the controller 129, and sixteen different polarization states of the light beam can be modulated, thus sixteen groups of intensity signals can be obtained, and corresponding measured Mueller-matrix data of the sample at each pixel on the camera 128 can be calculated. All of the intensity signals collected at each pixel of the camera 128 are analyzed to yield the measured Mueller-matrix data of the sample in the entire FOV. In addition, besides the analysis of each pixel on the camera 128, a plurality of pixels can be simultaneously analyzed so as to improve the SNR of the collected intensity signals.

5) The wavelength λ of the incident light beam is altered by the wavelength selector 102; a rotation angle of the plane mirror 107 is altered by rotating the sample stage 108; the light beam which was gathered at the back focal plane of the objective lens 116 is displaced, and an angle between the incident light beam projected from the objective lens 116 and the sample (which is the angle of incidence θ) is changed; the sample stage 118 is rotated to change an azimuth angle φ during the measurement (in terms of isotropic sample, the azimuth angle φ can be fixed at any angle); 2)-4) are repeated to obtain measured Mueller-matrix data under different wavelengths, different incident angles, and different azimuth angles.

6) Given the wavelength, the incident angle, and the azimuth angle, a theoretical Mueller matrix of the sample 117 is calculated according to the Fresnel formula.

Figure 2:
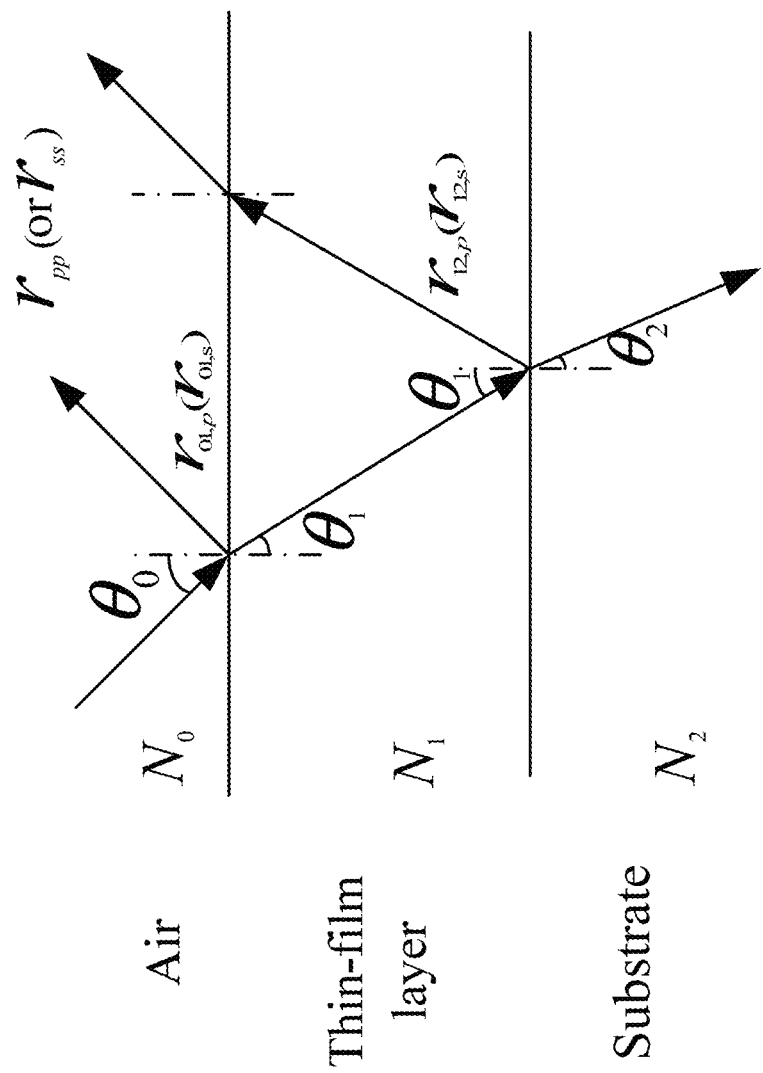
FIG. 2 is a diagram of a sample formed by a single thin film in accordance with one embodiment of the invention.

As shown in FIG. 2, an isotropic thin film is disposed on a substrate. A complex refractive index of the substrate is $N_2$, and a complex refractive index of the thin film is $N_1$. The thickness of the thin film is d. A refractive index of surrounding medium of the thin film is $N_0$, and when the surrounding medium is air, $N_0=1$. Complex refractive index N is defined as: N=n–ik, where n is refractive index of the medium, and k is an extinction coefficient of the medium; and i is an imaginary unit. Generally, the optical constant $N_1$ and the thickness d of the thin film are parameters to be measured. In the FIG. 2, $\theta_0$ represents an angle of incidence (the angle of incidence $\theta=\theta_0$). $\theta_1$ represents a refractive angle of the light beam after the light beam enters the thin film from the surrounding medium. $\theta_2$ represents a refractive angle of the light beam when the light beam enters the substrate from the thin film. According to the Fresnel law, a relationship between the optical constants is shown as Formula (5):

$$N_0 \sin\theta_0 = N_1 \sin\theta_1 = N_2 \sin\theta_2 \tag{5}$$

According to the Fresnel law, an expression of an amplitude reflection coefficient $r_{01,p}$ of p-polarized light (the p-polarized light is perpendicular to the plane of incidence) on an upper surface of the thin film, and an expression of an amplitude reflection coefficient $r_{01,s}$ of s-polarized light (the s-polarized light is parallel to the plane of incidence) on an upper surface of the thin film are shown as Formula (6) and Formula (7):

$$r_{01,p} = \frac{N_1\cos\theta_0 - N_0\cos\theta_1}{N_1\cos\theta_0 + N_0\cos\theta_1} \tag{6}$$

$$r_{01,s} = \frac{N_0\cos\theta_0 - N_1\cos\theta_1}{N_0\cos\theta_0 + N_1\cos\theta_1} \tag{7}$$

Similarly, according to the Fresnel law, an expression of an amplitude reflection coefficient $r_{12,p}$ of p-polarized light between the thin film and the substrate and an expression of an amplitude reflection coefficient $r_{12,s}$ of s-polarized light between the thin film and the substrate are shown as Formula (8) and Formula (9):

$$r_{12,p} = \frac{N_2\cos\theta_1 - N_1\cos\theta_2}{N_2\cos\theta_1 + N_1\cos\theta_2} \tag{8}$$

$$r_{12,s} = \frac{N_1\cos\theta_1 - N_2\cos\theta_2}{N_1\cos\theta_1 + N_2\cos\theta_2} \tag{9}$$

According to the Formulas (6)-(9), an expression of an amplitude reflection coefficient $r_{pp}$ of p-polarized light after the light beam is incident on the thin film sample and is reflected by the sample, and an expression of an amplitude reflection coefficient $r_{ss}$ of s-polarized light after the light beam is incident on the thin film sample and is reflected by the sample are shown as Formula (10) and Formula (11) (an amplitude reflection coefficient $r_{ps}=r_{sp}=0$):

$$r_{pp} = \frac{r_{01,p} + r_{12,p}\exp(-i2\beta)}{1 + r_{01,p}r_{12,p}\exp(-i2\beta)} \qquad (10)$$

$$r_{ss} = \frac{r_{01,s} + r_{12,s}\exp(-i2\beta)}{1 + r_{01,s}r_{12,s}\exp(-i2\beta)} \qquad (11)$$

where $\beta = 2\pi d N_1 \cos\theta_1/\lambda$, therefore, an amplitude ratio $\Psi$ and a phase difference $\Delta$ can be calculated according to the Formulas (10)-(11) in Formula (12):

$$\rho = \tan\Psi \exp(i\Delta) = \frac{r_{pp}}{r_{ss}} \qquad (12)$$

as the amplitude ratio $\Psi$ and the phase difference $\Delta$ are obtained, the Mueller matrix M of the sample 117 can be obtained in Formula (13):

$$M = R\begin{bmatrix} 1 & -\cos 2\Psi & 0 & 0 \\ -\cos 2\Psi & 1 & 0 & 0 \\ 0 & 0 & \sin 2\Psi \cos\Delta & \sin 2\Psi \sin\Delta \\ 0 & 0 & -\sin 2\Psi \sin\Delta & \sin 2\Psi \cos\Delta \end{bmatrix} \qquad (13)$$

where, $R=r_{ss}r_{ss}^* + r_{pp}r_{pp}^*)/2$, and R is the refractive index of the sample.

When the sample 117 is an anisotropy sample, correspondingly, the amplitude reflection coefficients $r_{ps}$ and $r_{sp}$ are not zero, and according to the Fresnel law or the 4×4 matrix method, a Jones matrix J of the sample 117 is shown as Formula (14):

$$J = \begin{bmatrix} r_{pp} & r_{ps} \\ r_{sp} & r_{ss} \end{bmatrix} \qquad (14)$$

when no depolarization effect exists during the measurement, according to a relationship between the Jones matrix and the Mueller matrix, the Mueller matrix M of the sample 117 is shown as Formula (15):

$$M = A(J \otimes J^*)A^{-1} \qquad (15)$$

where, $\otimes$ represents the Kronecker product, and J* is a complex conjugate matrix of the Jones matrix J; $A^{-1}$ is an inverse matrix of a matrix A, and the matrix A is shown as Formula (16):

$$A = \begin{bmatrix} 1 & 0 & 0 & 1 \\ 1 & 0 & 0 & -1 \\ 0 & 1 & 1 & 0 \\ 0 & i & -i & 0 \end{bmatrix} \qquad (16)$$

For more detailed content of the 4×4 matrix method, referring to M. Schubert, *Polarization-dependent optical parameters of arbitrarily anisotropic homogeneous layered systems*, Phys. Rev. B 53, 4265-4274 (1996), or the sixth chapter in *Spectroscopic Ellipsometry: Principles and Applications* written by H. Fujiwara.

7) The theoretical Mueller-matrix data in 6) is matched with the measured Mueller-matrix data of each pixel or each group of pixel in 5), and parameters of the thin film at each pixel is obtained thereby.

Parameter extraction process of the thin film is a typical solution of inverse problem. When measured Mueller-matrix data of the thin film is the input of the inverse problem, parameters of the thin film are supposed to be the output. The objective of the inverse problem is that the measured Mueller-matrix data on each pixel can find a group of parameter values of the thin film which makes it possible for the theoretical Mueller-matrix data to best match with the measured Mueller-matrix data at the pixel. The measured Mueller-matrix data at the pixel which is on arbitrary line m and row n of the camera 128 is taken as an example, and the solution process of the inverse problem is shown in Formula (17):

$$\hat{p} = \underset{p \in \Omega}{\operatorname{argmin}} \frac{1}{\sqrt{M-K-1}} \left\{ \sum_{i=1}^{N} \left[ \frac{y_{ex}(\lambda_i, \theta, \phi) - y_{cal}(p, \lambda_i, \theta, \phi)}{\delta y(\lambda_i)} \right]^2 \right\}^{1/2} \qquad (17)$$

where, $y_{ex}(\lambda_i, \theta, \phi)$ denotes the measured Mueller-matrix data obtained under the conditions of the ith (i=1, 2, ..., N) wavelength point, the angle of incidence $\theta$, and the azimuth angle $\phi$; $y_{cal}(p, \lambda_i, \theta, \phi)$ denotes the theoretical Mueller-matrix data obtained under the conditions of the wavelength $\lambda_i$, the incident angle $\theta$, and the azimuth angle $\phi$; p is a K-dimensional vector composed of parameters of the thin film; and $\Omega$ is the value range of the parameters; $\hat{p}$ is the final parameter value; $\delta y$ is the standard deviation of the measured data; and M is the total number of the data points; when the parameters to be measured are the amplitude ratio $\Psi$ and the phase difference $\Delta$, M=2N, and when the parameters to be measured are Mueller matrixes, M=15N. For solving the Formula (17), a non-liner regression method such the Levenberg-Marquardt algorithm is adopted.

By inputting the measured Mueller-matrix data at any pixel and solving the Formula (17), the parameter of the thin film at the pixel is obtained. The parameters of the thin film at all pixels form the three-dimensional microstructure of the thin film in the entire FOV.

Based on the above example, a method for in situ calibrating devices of the back focal plane Mueller-matrix microscope is provided, and examples of in situ calibration are also provided. The examples comprise in situ calibration example of the beam splitter 114 and in situ calibration example of the objective lens 116.

In situ calibration example of the beam splitter 114.

The beam splitter 114 in the polarizing unit allows the light beam to penetrate through, and in the analyzing unit is configured to reflect the light beam. An ideal non-polarization beam splitter does not the change the polarization state which means the amplitude ratio and the phase change when the beam splitter is configured to transmit light. In the measurement system, a theoretical Mueller matrix $M_t^{BS}$ of the ideal non-polarization beam splitter 114 when the beam splitter allows the light beam to penetrate through and a theoretical Mueller matrix $M_r^{BS}$ of the ideal non-polarization beam splitter when the beam splitter is configured to reflect the light beam are shown as Formula (18) and Formula (19):

$$M_t^{BS} = \begin{bmatrix} 1 & 0 & 0 & 0 \\ 0 & 1 & 0 & 0 \\ 0 & 0 & 1 & 0 \\ 0 & 0 & 0 & 1 \end{bmatrix} \quad (18)$$

$$M_r^{BS} = \begin{bmatrix} 1 & 0 & 0 & 0 \\ 0 & 1 & 0 & 0 \\ 0 & 0 & -1 & 0 \\ 0 & 0 & 0 & -1 \end{bmatrix} \quad (19)$$

Existing non-polarization beam splitter only optimizes the amplitude variation of the polarized components when the beam splitter transmits light, and gives no considerations to the phase change, resulting in obvious error during high-accuracy measurement by ellipsometry. To eliminate the adverse effect of the beam splitter 114 on the measurement accuracy, and improve the measurement accuracy of the device, the in situ calibration example is put forward so as to obtain the measured Mueller matrix $M_t^{BS'}$ of the non-polarization beam splitter 114 when the beam splitter allows the light beam to penetrate through and the measured Mueller matrix $M_r^{BS'}$ of the non-polarization beam splitter when the beam splitter is configured to reflect the light beam, and the results are input into the Formula (2).

Figure 3:
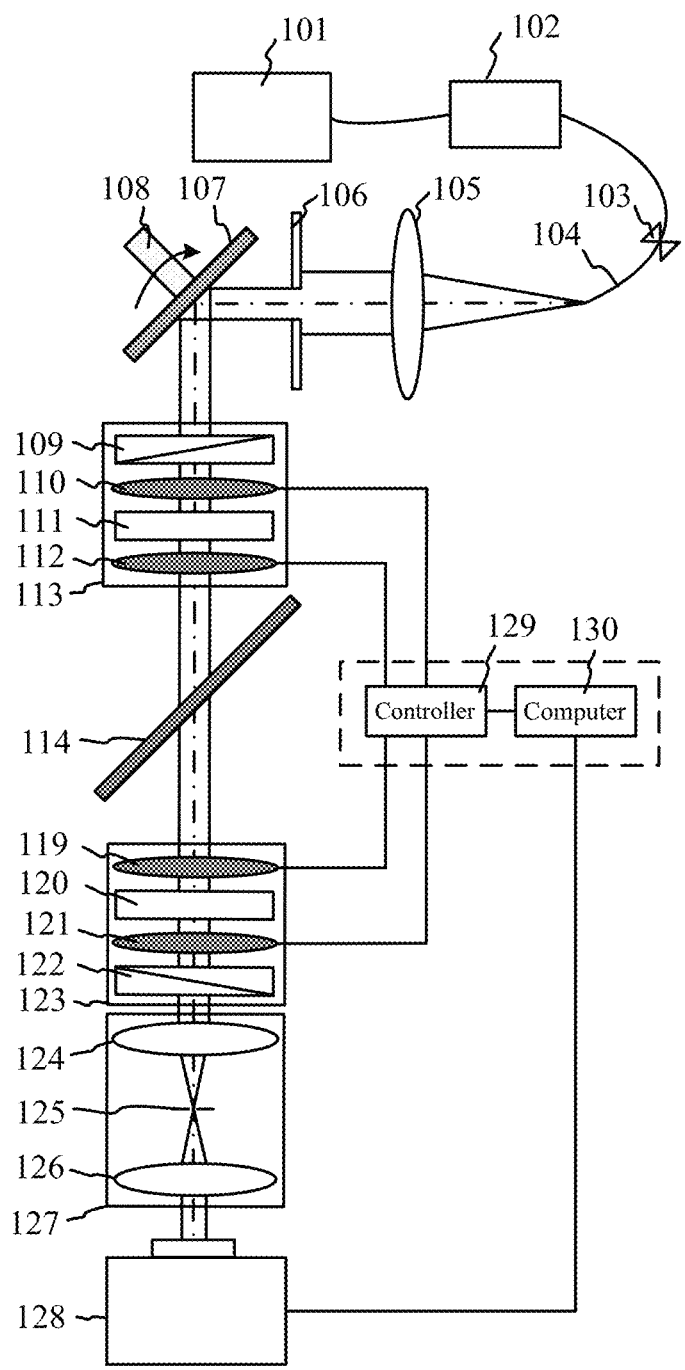
FIG. 3 is a first diagram showing a layout of devices in an in situ calibration example of a beam splitter.

FIG. 3 is a diagram showing a layout of devices in the in situ calibration example of the beam splitter 114 when the beam splitter allows light beam to penetrate through. As shown in FIG. 3, the in situ calibration example is based on a simplified light path unit structure of the Mueller-matrix ellipsometer; the beam splitter 114 replaced the sample 117, and is in situ measured to obtain the measured Mueller matrix $M_t^{BS'}$ of the beam splitter 114 when the beam splitter allows the light beam to penetrate through.

The single-wavelength light beam emitted from the external light source is collimated by the first lens 105 to yield single-wavelength collimated light beam which passes through the aperture diaphragm 106, and is reflected by the plane mirror 107. The light beam is modulated by the PSG 113 to yield polarized light beam. The polarized light beam is allowed to penetrate through the beam splitter and enters the PSA 123 where the polarization state of the light beam is analyzed. Then the light beam is allowed to pass through the BRS unit 127 and enter the camera 128.

Intensity signals of the reflected light are collected in the camera 128. The four ferroelectric liquid crystal devices in the PSG 113 and the PSA 123 are adjusted so as to obtain intensity signals under different polarization states.

A relationship between the Stokes vectors $S_{out}$ of the reflected light beam and the Stokes vectors $S_{in}$ of the incident light beam is shown as Formula (20):

$$S_{out} = [M_A R(\theta_A)] \cdot M(\theta_{F4}, \delta_{F4}) \cdot M(\theta_{C2}, \delta_{C2}) \cdot M(\theta_{F3}, \delta_{F3}) \\ \cdot M_t^{BS'} \cdot M(\theta_{F2}, \delta_{F2}) \cdot M(\theta_{C1}, \delta_{C1}) \cdot M(\theta_{F1}, \delta_{F1}) \cdot [R(-\theta_P) M_P] \cdot S_{in} \quad (20)$$

According to the Formulas (3) and (4) of the reflected light beam, Mueller-matrix elements at pixels of the camera 128 when the beam splitter allows the light beam to penetrate through are obtained based on the intensity signals of the reflected light under different polarization states collected by the camera 128. Intensity signals collected at all pixels of the camera 128 are analyzed to obtain a measured Mueller matrix of the beam splitter 114 in the entire FOV when the beam splitter allows the light beam to penetrate through. The wavelength of the incident light beam is altered via the wavelength selector 102, thus under the conditions of different wavelengths the measured Mueller matrix $M_t^{BS'}$ of the beam splitter 114 when the beam splitter allows the light beam to penetrate through is obtained.

Figure 4:
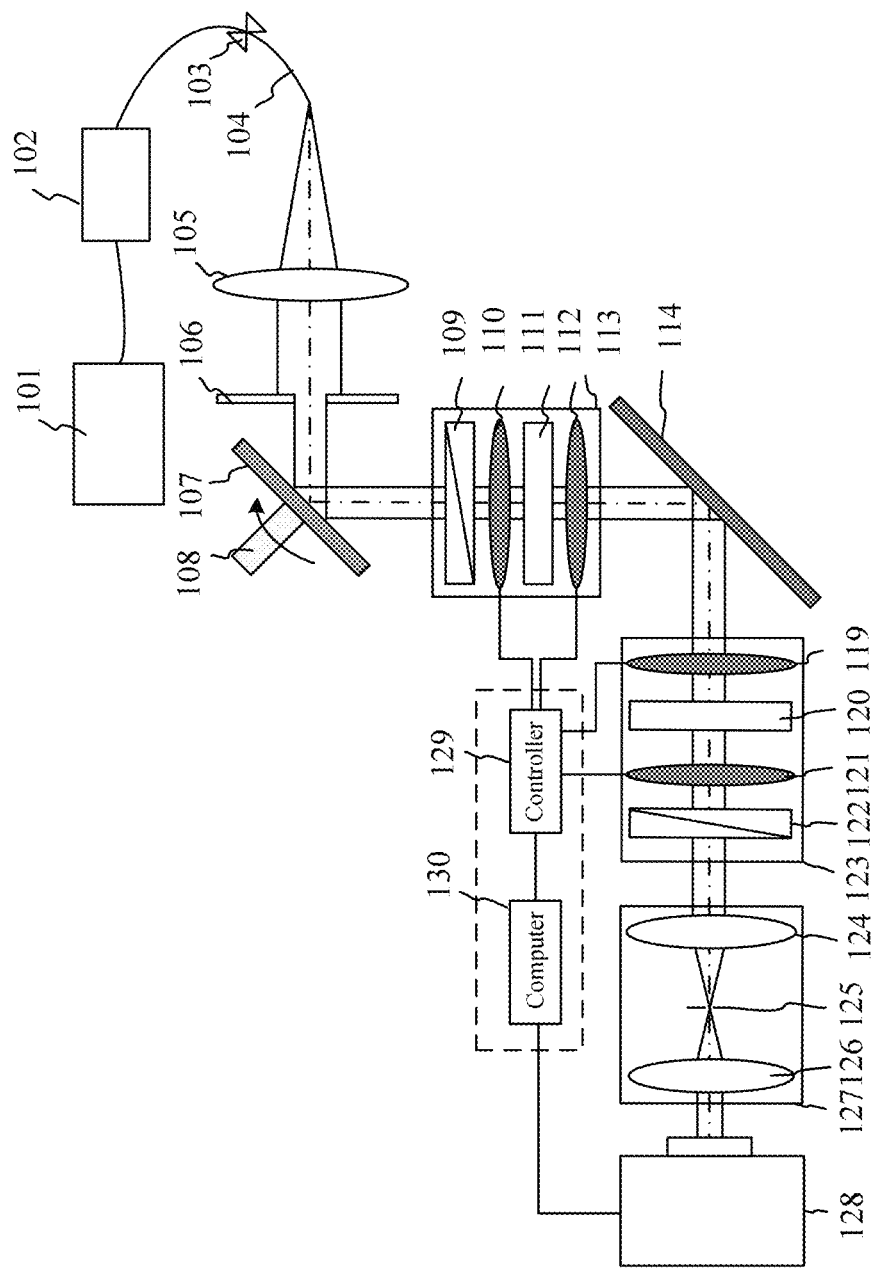
FIG. 4 is a second diagram showing a layout of devices in an in situ calibration example of a beam splitter.

FIG. 4 is a diagram showing a layout of devices in the in situ calibration example of the beam splitter 114 when the beam splitter is configured to reflect light. As shown in FIG. 4, the in situ calibration example of the beam splitter 114 is based on a simplified light path unit structure of the Mueller-matrix ellipsometer using the objective lens 116; the beam splitter 114 replaced the sample 117, and is in situ measured to obtain the measured Mueller matrix $M_r^{BS'}$ of the beam splitter 114 when the beam splitter is configured to reflect light beam.

The single-wavelength light beam emitted from the external light source is collimated by the first lens 105 to yield single-wavelength collimated light beam which passes through the aperture diaphragm 106, and is reflected by the plane mirror 107. The light beam is modulated by the PSG 113 to yield polarized light beam. The polarized light beam is reflected by the beam splitter 114 and enters the PSA 123 where the polarization state of the light beam is analyzed. Then the light beam is allowed to pass through the BRS unit 127 and enter the camera 128.

Intensity signals of the reflected light are collected in the camera 128. The four ferroelectric liquid crystal devices in the PSG 113 and the PSA 123 are adjusted so as to obtain intensity signals under different polarization states.

A relationship between the Stokes vectors $S_{out}$ of the reflected light beam and the Stokes vectors $S_{in}$ of the incident light beam is shown as Formula (21):

$$S_{out} = [M_A R(\theta_A)] \cdot M(\theta_{F4}, \delta_{F4}) \cdot M(\theta_{C2}, \delta_{C2}) \cdot M(\theta_{F3}, \delta_{F3}) \\ \cdot M_r^{BS'} \cdot M(\theta_{F2}, \delta_{F2}) \cdot M(\theta_{C1}, \delta_{C1}) \cdot M(\theta_{F1}, \delta_{F1}) \cdot [R(-\theta_P) M_P] \cdot S_{in} \quad (21)$$

According to the Formulas (3) and (4) of the reflected light beam, Mueller-matrix elements at pixels of the camera 128 when the beam-splitting plat is configured to reflect light beam are calculated based on the intensity signals of the reflected light under different polarization states collected by the camera 128. Intensity signals collected at all pixels of the camera 128 are analyzed to obtain the measured Mueller matrix of the beam splitter 114 in the entire FOV when the beam splitter is configured to reflect light. The wavelength of the incident light beam is altered via the wavelength selector 102, and an angle of reflection of the plane mirror 107 is altered via the rotating table 108, thus the measured Mueller matrix $M_r^{BS'}$ of the beam splitter 114 when the beam splitter is configured to reflect light beam can be obtained under different wavelengths and different angles of incidence.

In situ calibration example of the objective lens 116:

The objective lens 116 is configured to illuminate in the incident light path unit and collect the reflected light beam. The objective lens 116 has disadvantages as a great many of lenses which have difference in thickness, a wide angle of incidence, and complex coating materials, which tend to adversely affect the measurement accuracy. Although the adverse impact on the measurement accuracy has been taken into consideration when the objective lens 116 is designed and selected, the phase difference caused by the objective lens 116 still affects the measurement accuracy, therefore, the in situ calibration example of the objective lens 116 is put forward, and a spherical mirror 200 is used as a standard sample.

Figure 5:
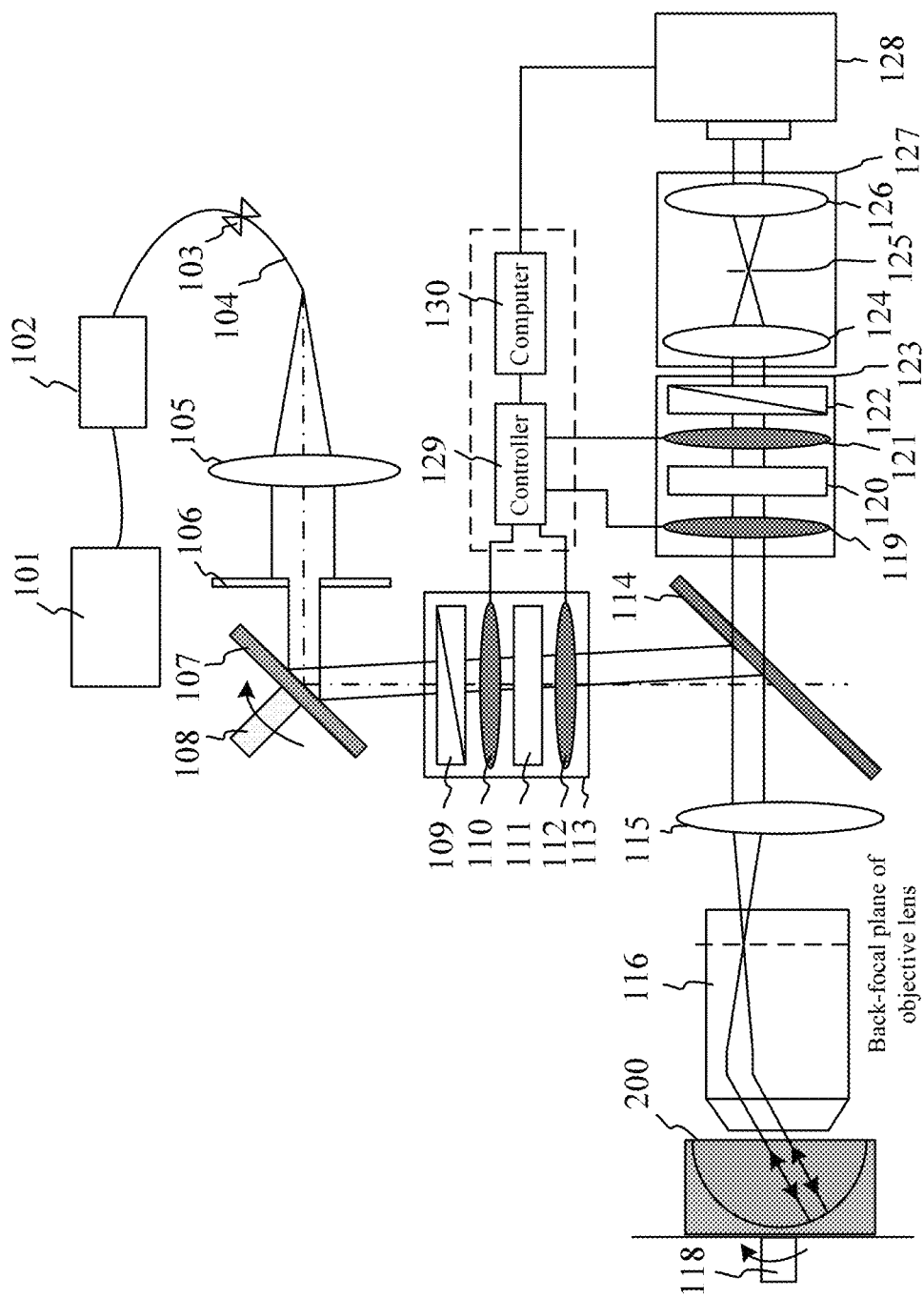
FIG. 5 is a first diagram showing a layout of devices in an in situ calibration example of an objective lens.

FIG. 5 is a diagram showing a layout of devices in the in situ calibration example of the objective lens 116 when the objective lens is configured to illuminate in the incident light path unit. As shown in FIG. 5, the in situ calibration example of the objective lens 116 is based on the structure of the Mueller-matrix ellipsometer, and the spherical mirror 200 replaces the sample 117 and is disposed on the sample stage 118 to be measured. The single-wavelength light beam emitted from the external light source is collimated by the first lens 105 to yield single-wavelength collimated light beam which passes through the aperture diaphragm 106, and is reflected by the plane mirror 107. The light beam is modulated by the polarization generation unit 113 to yield polarized light beam. The polarized light beam is reflected by the beam splitter 114 and is gathered at the back focal plane of the objective lens 116 by the second lens 115. Because the center of the spherical mirror 200 is on the front focus plane of the objective lens 116, the light beam is vertically incident on the spherical surface from the objective lens 116. Due to the characteristics of the spherical mirror 200, the light beam is reflected back the same light path and is collected by the objective lens 116. The reflected light beam is allowed to penetrate through the second lens 115 and the beam splitter 114, and enters the PSA 123 where the polarization state of the light beam is analyzed. Then the light beam is allowed to pass through the BRS unit 127 and enter the camera 128.

In the measurement system, the objective lens 116 and the spherical mirror 200 are as a whole and used as a substitution for the sample 117, and an expression of a measured Mueller matrix $M_{id}^m$ thereof is shown as Formula (22):

$$M_{id}^m = M_{id}^{OB} M_{SM} M_{id}^{OB} \quad (22)$$

where, $M_{id}^{OB}$ is the measured Mueller matrix of the objective lens 116 when the objective lens is configured to illuminate in the incident light path unit; $M_{SM}$ is the Mueller matrix of the spherical mirror 200 when the light beam is vertically incident on the spherical surface, and the value thereof equals to the value of the Mueller matrix of the thin film when the light beam is vertically incident on the thin film, as the amplitude value and the phase difference are not directly changed, the measured Mueller matrix denotes the change of polarization state before and after the polarized light beam passes through the objective lens 116. The measured Mueller matrix $M_{id}^m$ can be obtained using the method in the mentioned example, and the measured Mueller matrix $M_{id}^{OB}$ of the objective lens 116 when the objective lens is configured to illuminate in the incident light path unit can be calculated according to the Formula (22).

Figure 6:
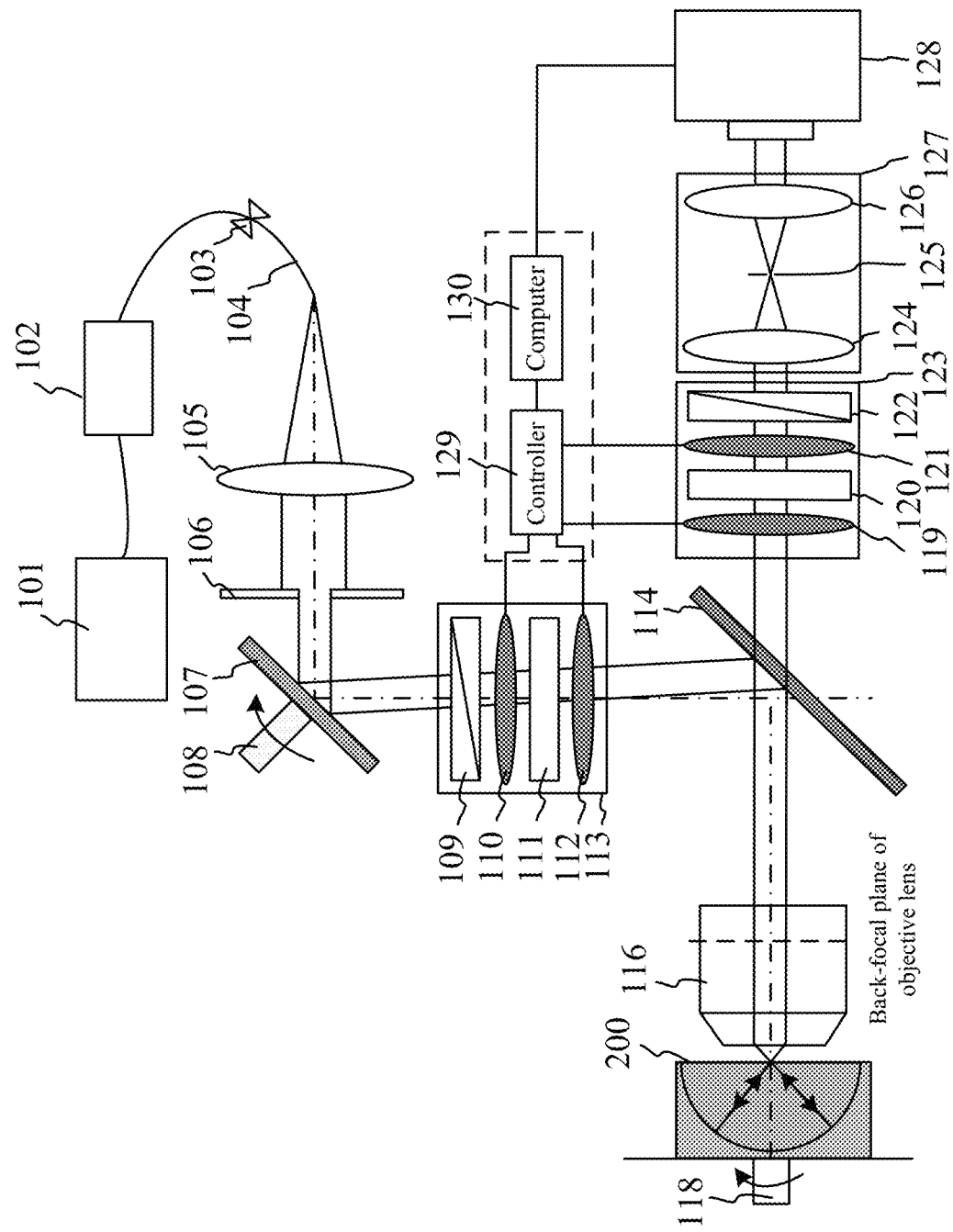
FIG. 6 is a second diagram showing a layout of devices in an in situ calibration example of an objective lens.

FIG. 6 is a diagram showing a layout of devices in the in situ calibration example of the objective lens 116 when the objective lens is configured to collect reflected light. As shown in FIG. 6, the in situ calibration example of the objective lens 116 is based on the structure of the back focal plane Mueller-matrix microscope, and the second lens 116 is removed, so that the light beams which are incident on the center of the back focal plane of the objective lens 116 are in parallel, in addition, the spherical mirror 200 replaces the sample 117 and is disposed on the sample stage 118 to be measured.

The single-wavelength light beams emitted from the external light source are collimated by the first lens 105 to yield single-wavelength collimated light beams which pass through the aperture diaphragm 106, and are reflected by the plane mirror 107. The light beams are modulated by the PSG 113 to yield polarized light beams. The polarized light beams are reflected by the beam splitter and are incident on a center of the back focal plane of the objective lens 116 in parallel. Because the center of the spherical mirror 200 is on the front focal plane of the objective lens 116, the light beams are vertically incident on the spherical surface of the spherical mirror 200 from the objective lens 116. Due to the characteristics of the spherical mirror 200, the light beams are reflected back the same light path and are collected by the objective lens 116. The reflected light beams are allowed to penetrate through the beam splitter 114, and enter the PSA 123 where the polarization state of the light beams is analyzed. Then the light beams are allowed to pass through the BRS unit 127 and enter the camera 128.

In the measurement system, the objective lens 116 and the spherical mirror 200 are as a whole and used as a substitution for the sample 117, and an expression of the measured Mueller matrix $M_{rd}^m$ thereof is shown as Formula (23):

$$M_{rd}^m = M_{rd}^{OB} M_{SM} M_{rd}^{OB} \quad (23)$$

where, $M_{rd}^{OB}$ is the measured Mueller matrix of the objective lens 116 when the objective lens is configured to collect reflected light; $M_{SM}$ is the Mueller matrix of the spherical mirror when the light beam is vertically incident on the spherical surface, and the value thereof equals to the value of the Mueller matrix of the thin film when the light beam is vertically incident on the thin film; as the amplitude value and the phase difference are not directly changed, the measured Mueller matrix denotes the change of polarization state before and after the polarized light beam passes through the objective lens 116. The measured Mueller matrix $M_{rd}^m$ can be obtained using the method in the mentioned example, thus the measured Mueller matrix $M_{rd}^{OB}$ of the objective lens 116 when the objective lens is configured to collect reflected light can be calculated according to the Formula (23).

In the in situ calibration example of the objective lens 116 in the back focal plane Mueller-matrix microscope, the rotating table 108 is rotated to control the angle of reflection of the plane mirror 107, so as to change the angle of incidence (θ), and the measured Mueller matrix of the objective lens 116 when the objective lens is in the incident light path unit and the measured Mueller matrix of the objective lens when the objective lens is configured to collect reflected light are respectively calculated. The wavelength λ of the light beams is altered via the wavelength selector 102, thus under different wavelengths the measured Mueller matrix $M_{id}^{OB}$ of the objective lens 116 when the objective is in the incident light path unit and the measured Mueller matrix $M_{rd}^{OB}$ of the objective lens when the objective lens is configured to collect reflected light can be obtained.

The ellipsometer capable of phase modulation using liquid crystal devices can satisfy the requirements for measurement, and can completely eliminate optical motion elements in the optical path unit. The vertical objective lens structure of the optical microscope is used by the ellipsometer for reference, thus the problems as small focal depth and narrow FOV of illumination-tilted specular-reflection imaging system are avoided, meanwhile, the objective lens 116 and the BRS unit 127 are used, thus a high-resolution, wild FOV, contactless, rapid, non-destructive, and accurate measurement of geometric parameters of the 2D materials is realized.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A Mueller-matrix microscope, comprising:
an external light source module, the external source module comprising a light source, a wavelength selector, an optical fiber coupler, and an output optical fiber;
a polarizing unit, the polarizing unit comprising a first lens, an aperture diaphragm, a plane mirror, a polarization state generator (PSG), a beam splitter, a second lens, and an objective lens, and the PSG comprising a polarizer, a first ferroelectric liquid crystal device, a first quarter-wave plate, and a second ferroelectric liquid crystal device;
an analyzing unit, the analyzing unit comprising a polarization state analyzer (PSA) and a backside reflection suppression (BRS) unit, the PSA comprising a third ferroelectric liquid crystal device, a second quarter-wave plate, a fourth ferroelectric liquid crystal device, and an analyzer, and the BRS unit comprises a third lens, a pinhole, and a fourth lens;
a controller;
a computer;
a sample stage; and
a camera;
wherein
the external source module, the wave selector, and the optical fiber coupler are connected in sequence through optical fibers;
the optical fiber coupler is connected to the output optical fiber;
an output end of the output optical fiber, the first lens, the aperture diaphragm, the plane mirror, the polarizer, the first ferroelectric liquid crystal device, the first quarter-wave plate, the second ferroelectric liquid crystal device, the beam splitter, the second lens, the objective lens, and the sample stage are disposed in order to form an optical path;
the second lens is disposed at a frontside of the beam splitter;
the polarizer, the first ferroelectric liquid crystal device, the first quarter-wave plate, and the second ferroelectric liquid crystal device are disposed coaxially along the optical path;
the PSA is aligned with the BRS unit;
the PSA and the BRS unit are dispose at a backside of the beam splitter;
the third ferroelectric liquid crystal device, the second quarter-wave plate, the fourth ferroelectric liquid crystal device, the analyzer, the third lens, the pinhole, and the fourth lens are aligned in that order at the backside of the beam splitter;
the first ferroelectric liquid crystal device and the second ferroelectric liquid crystal device are connected to the controller;
the third ferroelectric liquid crystal device and the fourth ferroelectric liquid crystal device are connected to the controller;
the controller and the camera are connected to the computer; and
the camera is disposed at a back focal plane of the fourth lens;
when in use,
the polarizing unit modulates a light beam emitted from the external light source module to yield a polarized light beam, and then projects the polarized light beam on a surface of a sample disposed on the sample support to be measured; and
the analyzing unit analyzes the polarized light beam reflected from the surface of the sample and acquires information of the sample.

2. The microscope of claim 1, wherein when in use, the light beam emitted from the external light source module is collimated by the first lens to yield a collimated light beam; the collimated light beam is allowed to pass through the aperture diaphragm, and is specularly reflected by the plane mirror; the reflected light beam enters the polarization generation unit and is modulated to yield the polarized light beam; and the polarized light beam is allowed to pass through the beam splitter, the second lens, and the objective lens, in that order, and then is projected on the surface of the sample.

3. The microscope of claim 2, wherein the plane mirror is disposed on a rotating table.

4. The microscope of claim 2, wherein the beam splitter is configured to reflect the light beam in the polarizing unit to change a direction of propagation of the light beam, meanwhile, the beam splitter is configured to allow the light beam to penetrate through in the analyzing unit; and the beam splitter is a non-polarization beam splitter.

5. The microscope of claim 2, wherein when in use, the light beam reflected from the surface of the sample is collected by the objective lens, and passes through the second lens, the beam splitter, the PSA unit, and the BRS unit, in that order, and then enters the camera; the PSA unit is configured to demodulate the polarization state of the light beam; and the BRS unit is configured to suppress the backside reflections from transparent substrate.

6. The microscope of claim 5, wherein focal lengths of the third lens and the fourth lens are conjugate; the pinhole is disposed at a conjugate focus of the third lens and the fourth lens.

7. The microscope of claim 1, wherein the light beam generated by the light source is selected by the wavelength selector to yield a single-wavelength light beam; the single-wavelength light beam is transmitted to the output optical fiber via the optical fiber coupler; and the output optical fiber is used as an output end of the external light source module.

8. A method for measuring a sample using the microscope of claim 1, the method comprising:
1) placing the sample at the sample stage; regulating the polarizing unit and the analyzing unit to obtain an image of an area of the sample at the camera;
2) collimating a single-wavelength light beam emitted from the external light source module to yield a collimated light beam; modulating the collimated light beam using the PSG to yield elliptically polarized light; and projecting the polarized light on the surface of the sample;
3) demodulating the light beam reflected from the surface of the sample using the PSA; and allowing the light beam to enter the camera to obtain different intensity signals of the light beam under different polarization states;
4) calculating measured Mueller-matrix data of the sample at each pixel on the camera according to the intensity signals in 3), all the measured Mueller-matrix data at each pixel form measured Mueller-matrix data of the sample in an entire field of view (FOV);
5) changing a wavelength $\lambda$ and an angle of incidence $\theta$ of the light beam; rotating the sample stage and altering an azimuth angle $\phi$ between the light beam and the sample; repeating 2)-4), and calculating the measured Mueller-matrix data under different wavelengths λ, different angles of incidence θ, and different azimuth angles φ;

6) calculating theoretical Mueller-matrix data of the sample according to a Fresnel formula based on a given configuration of the wavelength λ, the angle of incidence θ, and the azimuth angle φ; and 7) fitting the measured Mueller-matrix data to obtain actual Mueller-matrix data of the sample; comparing the actual Mueller-matrix data with the theoretical Mueller-matrix data: when a deviation between the actual Mueller-matrix data and the theoretical Mueller-matrix data falls within a given range, confirming the actual Mueller-matrix data is accurate; calculating parameter values of the sample at each pixel according to the actual Mueller-matrix data; calculating parameter values of the sample at all pixels to obtain a three-dimensional microstructure of the sample in the entire FOV; when the deviation is out of the given range, repeating 2)-6) until the deviation between the actual Mueller-matrix data and the theoretical Mueller-matrix data falls within the given range, obtaining the three-dimensional microstructure of the sample.

9. An in situ calibration method of a beam splitter and an objective lens using the microscope of claim 1, the method comprising:

1) calibrating a Muller matrix of the beam splitter when the beam splitter is configured to allow a light beam to penetrate through and reflect the light beam; and 2) calibrating a Muller matrix of the objective lens when the objective lens is configured to illuminate in an incident light path unit and collect a reflected light beam.

* * * * *